(12) United States Patent
Okazaki et al.

(10) Patent No.: US 8,450,123 B2
(45) Date of Patent: May 28, 2013

(54) OXYGEN DIFFUSION EVALUATION METHOD OF OXIDE FILM STACKED BODY

(75) Inventors: Yutaka Okazaki, Kanagawa (JP);
Keitaro Imai, Kanagawa (JP); Atsuo Isobe, Kanagawa (JP); Shunpei Yamazaki, Tokyo (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 33 days.

(21) Appl. No.: 13/213,458

(22) Filed: Aug. 19, 2011

(65) Prior Publication Data

US 2012/0214259 A1   Aug. 23, 2012

(30) Foreign Application Priority Data

Aug. 27, 2010   (JP) ................. 2010-190577

(51) Int. Cl.
*H01L 21/66*   (2006.01)
(52) U.S. Cl.
USPC ...................... 438/14; 257/E21.53
(58) Field of Classification Search
USPC ...................... 438/14; 257/E21.53
See application file for complete search history.

(56) References Cited

U.S. PATENT DOCUMENTS

| | | |
|---|---|---|
| 5,731,856 A | 3/1998 | Kim et al. |
| 5,744,864 A | 4/1998 | Cillessen et al. |
| 6,294,274 B1 | 9/2001 | Kawazoe et al. |
| 6,563,174 B2 | 5/2003 | Kawasaki et al. |
| 6,727,522 B1 | 4/2004 | Kawasaki et al. |
| 7,049,190 B2 | 5/2006 | Takeda et al. |
| 7,061,014 B2 | 6/2006 | Hosono et al. |
| 7,064,346 B2 | 6/2006 | Kawasaki et al. |
| 7,105,868 B2 | 9/2006 | Nause et al. |
| 7,211,825 B2 | 5/2007 | Shih et al |
| 7,282,782 B2 | 10/2007 | Hoffman et al. |

(Continued)

FOREIGN PATENT DOCUMENTS

| | | |
|---|---|---|
| EP | 1737044 A | 12/2006 |
| EP | 2226847 A | 9/2010 |

(Continued)

OTHER PUBLICATIONS

Matsumoto et al., "Oxygen diffusion in zinc-oxide thin films prepared by pulsed-laser deposition," J. Ceram. Soc. Japan. (Journal of the Ceramic Society of Japan), 2009, vol. 117, No. 5, pp. 666-670.

(Continued)

*Primary Examiner* — Kimberly Rizkallah
*Assistant Examiner* — Marvin Payen
(74) *Attorney, Agent, or Firm* — Eric J. Robinson; Robinson Intellectual Property Law Office, P.C.

(57) ABSTRACT

Experience shows that, in a material containing oxygen as a main component, an excess or deficiency of trace amounts of oxygen with respect to a stoichiometric composition, or the like affects properties of the material. An oxygen diffusion evaluation method of an oxide film stacked body includes the steps of: measuring a quantitative value of one of oxygen isotopes of a substrate including a first oxide film and a second oxide film which has an existence proportion of an oxygen isotope different from an existence proportion of an oxygen isotope in the first oxide film in a depth direction, by secondary ion mass spectrometry; and evaluating the one of the oxygen isotopes diffused from the first oxide film to the second oxide film.

18 Claims, 7 Drawing Sheets

U.S. PATENT DOCUMENTS

| | | | |
|---|---|---|---|
| 7,297,977 | B2 | 11/2007 | Hoffman et al. |
| 7,323,356 | B2 | 1/2008 | Hosono et al. |
| 7,385,224 | B2 | 6/2008 | Ishii et al. |
| 7,402,506 | B2 | 7/2008 | Levy et al. |
| 7,411,209 | B2 | 8/2008 | Endo et al. |
| 7,453,065 | B2 | 11/2008 | Saito et al. |
| 7,453,087 | B2 | 11/2008 | Iwasaki |
| 7,462,862 | B2 | 12/2008 | Hoffman et al. |
| 7,468,304 | B2 | 12/2008 | Kaji et al. |
| 7,501,293 | B2 | 3/2009 | Ito et al. |
| 7,674,650 | B2 | 3/2010 | Akimoto et al. |
| 7,732,819 | B2 | 6/2010 | Akimoto et al. |
| 2001/0046027 | A1 | 11/2001 | Tai et al. |
| 2002/0056838 | A1 | 5/2002 | Ogawa |
| 2002/0132454 | A1 | 9/2002 | Ohtsu et al. |
| 2003/0189401 | A1 | 10/2003 | Kido et al. |
| 2003/0218222 | A1 | 11/2003 | Wager et al. |
| 2004/0038446 | A1 | 2/2004 | Takeda et al. |
| 2004/0127038 | A1 | 7/2004 | Carcia et al. |
| 2005/0017302 | A1 | 1/2005 | Hoffman |
| 2005/0199959 | A1 | 9/2005 | Chiang et al. |
| 2006/0035452 | A1 | 2/2006 | Carcia et al. |
| 2006/0043377 | A1 | 3/2006 | Hoffman et al. |
| 2006/0091793 | A1 | 5/2006 | Baude et al. |
| 2006/0108529 | A1 | 5/2006 | Saito et al. |
| 2006/0108636 | A1 | 5/2006 | Sano et al. |
| 2006/0110867 | A1 | 5/2006 | Yabuta et al. |
| 2006/0113536 | A1 | 6/2006 | Kumomi et al. |
| 2006/0113539 | A1 | 6/2006 | Sano et al. |
| 2006/0113549 | A1 | 6/2006 | Den et al. |
| 2006/0113565 | A1 | 6/2006 | Abe et al. |
| 2006/0169973 | A1 | 8/2006 | Isa et al. |
| 2006/0170111 | A1 | 8/2006 | Isa et al. |
| 2006/0197092 | A1 | 9/2006 | Hoffman et al. |
| 2006/0208977 | A1 | 9/2006 | Kimura |
| 2006/0228974 | A1 | 10/2006 | Thelss et al. |
| 2006/0231882 | A1 | 10/2006 | Kim et al. |
| 2006/0238135 | A1 | 10/2006 | Kimura |
| 2006/0244107 | A1 | 11/2006 | Sugihara et al. |
| 2006/0284171 | A1 | 12/2006 | Levy et al. |
| 2006/0284172 | A1 | 12/2006 | Ishii |
| 2006/0292777 | A1 | 12/2006 | Dunbar |
| 2007/0024187 | A1 | 2/2007 | Shin et al. |
| 2007/0046191 | A1 | 3/2007 | Saito |
| 2007/0052025 | A1 | 3/2007 | Yabuta |
| 2007/0054507 | A1 | 3/2007 | Kaji et al. |
| 2007/0090365 | A1 | 4/2007 | Hayashi et al. |
| 2007/0108446 | A1 | 5/2007 | Akimoto |
| 2007/0152217 | A1 | 7/2007 | Lai et al. |
| 2007/0172591 | A1 | 7/2007 | Seo et al. |
| 2007/0187678 | A1 | 8/2007 | Hirao et al. |
| 2007/0187760 | A1 | 8/2007 | Furuta et al. |
| 2007/0194379 | A1 | 8/2007 | Hosono et al. |
| 2007/0252928 | A1 | 11/2007 | Ito et al. |
| 2007/0272922 | A1 | 11/2007 | Kim et al. |
| 2007/0287296 | A1 | 12/2007 | Chang |
| 2008/0006877 | A1 | 1/2008 | Mardilovich et al. |
| 2008/0038882 | A1 | 2/2008 | Takechi et al. |
| 2008/0038929 | A1 | 2/2008 | Chang |
| 2008/0050595 | A1 | 2/2008 | Nakagawara et al. |
| 2008/0073653 | A1 | 3/2008 | Iwasaki |
| 2008/0083950 | A1 | 4/2008 | Pan et al. |
| 2008/0106191 | A1 | 5/2008 | Kawase |
| 2008/0128689 | A1 | 6/2008 | Lee et al. |
| 2008/0129195 | A1 | 6/2008 | Ishizaki et al. |
| 2008/0166834 | A1 | 7/2008 | Kim et al. |
| 2008/0182358 | A1 | 7/2008 | Cowdery-Corvan et al. |
| 2008/0224133 | A1 | 9/2008 | Park et al. |
| 2008/0254569 | A1 | 10/2008 | Hoffman et al. |
| 2008/0258139 | A1 | 10/2008 | Ito et al. |
| 2008/0258140 | A1 | 10/2008 | Lee et al. |
| 2008/0258141 | A1 | 10/2008 | Park et al. |
| 2008/0258143 | A1 | 10/2008 | Kim et al. |
| 2008/0296568 | A1 | 12/2008 | Ryu et al. |
| 2009/0068773 | A1 | 3/2009 | Lai et al. |
| 2009/0073325 | A1 | 3/2009 | Kuwabara et al. |
| 2009/0114910 | A1 | 5/2009 | Chang |
| 2009/0134399 | A1 | 5/2009 | Sakakura et al. |
| 2009/0152506 | A1 | 6/2009 | Umeda et al. |
| 2009/0152541 | A1 | 6/2009 | Maekawa et al. |
| 2009/0278122 | A1 | 11/2009 | Hosono et al. |
| 2009/0280600 | A1 | 11/2009 | Hosono et al. |
| 2010/0065844 | A1 | 3/2010 | Tokunaga |
| 2010/0092800 | A1 | 4/2010 | Itagaki et al. |
| 2010/0109002 | A1 | 5/2010 | Itagaki et al. |

FOREIGN PATENT DOCUMENTS

| | | |
|---|---|---|
| JP | 60-198861 A | 10/1985 |
| JP | 63-210022 A | 8/1988 |
| JP | 63-210023 A | 8/1988 |
| JP | 63-210024 A | 8/1988 |
| JP | 63-215519 A | 9/1988 |
| JP | 63-239117 A | 10/1988 |
| JP | 63-265818 A | 11/1988 |
| JP | 05-251705 A | 9/1993 |
| JP | 08-264794 A | 10/1996 |
| JP | 11-505377 | 5/1999 |
| JP | 2000-044236 A | 2/2000 |
| JP | 2000-150900 A | 5/2000 |
| JP | 2002-076356 A | 3/2002 |
| JP | 2002-289859 A | 10/2002 |
| JP | 2003-086000 A | 3/2003 |
| JP | 2003-086808 A | 3/2003 |
| JP | 2004-103957 A | 4/2004 |
| JP | 2004-273614 A | 9/2004 |
| JP | 2004-273732 A | 9/2004 |
| JP | 2006-165528 A | 6/2006 |
| WO | WO-2004/114391 | 12/2004 |

OTHER PUBLICATIONS

Fortunato.E et al., "Wide-Bandgap High-Mobility ZNO Thin-Film Transistors Produced at Room Temperature,", Appl. Phys. Lett. (Applied Physics Letters), Sep. 27, 2004, vol. 85, No. 13, pp. 2541-2543.

Dembo.H et al., "RFCPUS on Glass and Plastic Substrates Fabricated by TFT Transfer Technology,", IEDM 05: Technical Digest of International Electron Devices Meeting, Dec. 5, 2005, pp. 1067-1069.

Ikeda.T et al., "Full-Functional System Liquid Crystal Display Using CG-Silicon Technology,", SID Digest '04 : SID International Symposium Digest of Technical Papers, 2004, vol. 35, pp. 860-863.

Nomura.K et al., "Room-Temperature Fabrication of Transparent Flexible Thin-Film Transistors Using Amorphous Oxide Semiconductors,", Nature, Nov. 25, 2004, vol. 432, pp. 488-492.

Park.J et al., "Improvements in the Device Characteristics of Amorphous Indium Gallium Zinc Oxide Thin-Film Transistors by Ar Plasma Treatment,", Appl. Phys. Lett. (Applied Physics Letters), Jun. 26, 2007, vol. 90, No. 26, pp. 262106-1-262106-3.

Takahashi.M et al., "Theoretical Analysis of IGZO Transparent Amorphous Oxide Semiconductor,", IDW '08 : Proceedings of the 15th International Display Workshops, Dec. 3, 2008, pp. 1637-1640.

Hayashi.R et al., "42.1: Invited Paper: Improved Amorphous In—Ga—Zn—O TFTs,", SID Digest '08 : SID International Symposium Digest of Technical Papers, May 20, 2008, vol. 39, pp. 621-624.

Prins.M et al., "A Ferroelectric Transparent Thin-Film Transistor,", Appl. Phys. Lett. (Applied Physics Letters), Jun. 17, 1996, vol. 68, No. 25, pp. 3650-3652.

Nakamura.M et al., "The phase relations in the In2O3-Ga2ZnO4-ZnO system at 1350° C,", Journal of Solid State Chemistry, Aug. 1, 1991, vol. 93, No. 2, pp. 298-315.

Kimizuka.N. et al., "Syntheses and Single-Crystal Data of Homologous Compounds, In2O3(ZnO)m (m = 3, 4, and 5), InGaO3(ZnO)3, and Ga2O3(ZnO)m (m = 7, 8, 9,and 16) in the In2O3-ZnGa2O4-ZnO System,", Journal of Solid State Chemistry, Apr. 1, 1995, vol. 116, No. 1, pp. 170-178.

Nomura.K et al., "Thin-Film Transistor Fabricated in Single-Crystalline Transparent Oxide Semiconductor,", Science, May 23, 2003, vol. 300, No. 5623, pp. 1269-1272.

Masuda.S et al., "Transparent thin film transistors using ZnO as an active channel layer and their electrical properties,", J. Appl. Phys. (Journal of Applied Physics), Feb. 1, 2003, vol. 93, No. 3, pp. 1624-1630.

Asakuma.N. et al., "Crystallization and Reduction of Sol-Gel-Derived Zinc Oxide Films by Irradiation With Ultraviolet Lamp,", Journal of Sol-Gel Science and Technology, 2003, vol. 26, pp. 181-184.
Osada.T et al., "15.2: Development of Driver-Integrated Panel using Amorphous In—Ga—Zn-Oxide TFT,", SID Digest '09 : SID International Symposium Digest of Technical Papers, May 31, 2009, pp. 184-187.
Nomura.K et al., "Carrier transport in transparent oxide semiconductor with intrinsic structural randomness probed using single-crystalline InGaO3(ZnO)5 films,", Appl. Phys. Lett. (Applied Physics Letters) , Sep. 13, 2004, vol. 85, No. 11, pp. 1993-1995.
Li.C et al., "Modulated Structures of Homologous Compounds InMO3(ZnO)m (M=In,Ga; m=Integer) Described by Four-Dimensional Superspace Group,", Journal of Solid State Chemistry, 1998, vol. 139, pp. 347-355.
Son.K et al., "42.4L: Late-News Paper: 4 Inch QVGA AMOLED Driven by the Threshold Voltage Controlled Amorphous GIZO (Ga2O3-In2O3-ZnO) TFT,", SID Digest '08 : SID International Symposium Digest of Technical Papers, May 20, 2008, vol. 39, pp. 633-636.
Lee.J et al., "World's Largest (15-Inch) XGA AMLCD Panel Using IGZO Oxide TFT,", SID Digest '08 : SID International Symposium Digest of Technical Papers, May 20, 2008, vol. 39, pp. 625-628.
Nowatari.H et al., "60.2: Intermediate Connector With Suppressed Voltage Loss for White Tandem OLEDS,", SID Digest '09 : SID International Symposium Digest of Technical Papers, May 31, 2009, vol. 40, pp. 899-902.
Kanno.H et al., "White Stacked Electrophosphorecent Organic Light-Emitting Devices Employing MOO3 as a Charge-Generation Layer,", Adv. Mater. (Advanced Materials), 2006, vol. 18, No. 3, pp. 339-342.
Tsuda.K et al., "Ultra Low Power Consumption Technologies for Mobile TFT-LCDs ,", IDW '02 : Proceedings of the 9th International Display Workshops, Dec. 4, 2002, pp. 295-298.
Van de Walle.C, "Hydrogen as a Cause of Doping in Zinc Oxide,", Phys. Rev. Lett. (Physical Review Letters), Jul. 31, 2000, vol. 85, No. 5, pp. 1012-1015.
Fung.T et al., "2-D Numerical Simulation of High Performance Amorphous In—Ga—Zn—O TFTs for Flat Panel Displays,", AM-FPD '08 Digest of Technical Papers, Jul. 2, 2008, pp. 251-252, The Japan Society of Applied Physics.
Jeong.J et al., "3.1: Distinguished Paper: 12.1-Inch WXGA AMOLED Display Driven by Indium-Gallium-Zinc Oxide TFTs Array,", SID Digest '08 : SID International Symposium Digest of Technical Papers, May 20, 2008, vol. 39, No. 1, pp. 1-4.
Park.J et al., "High performance amorphous oxide thin film transistors with self-aligned top-gate structure,", IEDM 09: Technical Digest of International Electron Devices Meeting, Dec. 7, 2009, pp. 191-194.
Kurokawa.Y et al., "UHF RFCPUS on Flexible and Glass Substrates for Secure RFID Systems,", Journal of Solid-State Circuits , 2008, vol. 43, No. 1, pp. 292-299.
Ohara.H et al., "Amorphous In—Ga—Zn-Oxide TFTs with Suppressed Variation for 4.0 inch QVGA AMOLED Display,", AM-FPD '09 Digest of Technical Papers, Jul. 1, 2009, pp. 227-230, The Japan Society of Applied Physics.
Coates.D et al., "Optical Studies of the Amorphous Liquid-Cholesteric Liquid Crystal Transition:The "Blue Phase",", Physics Letters, Sep. 10, 1973, vol. 45A, No. 2, pp. 115-116.
Cho.D et al., "21.2:Al and Sn-Doped Zinc Indium Oxide Thin Film Transistors for AMOLED Back-Plane,", SID Digest '09 : SID International Symposium Digest of Technical Papers, May 31, 2009, pp. 280-283.
Lee.M et al., "15.4:Excellent Performance of Indium-Oxide-Based Thin-Film Transistors by DC Sputtering,", SID Digest '09 : SID International Symposium Digest of Technical Papers, May 31, 2009, pp. 191-193.
Jin.D et al., "65.2:Distinguished Paper:World-Largest (6.5") Flexible Full Color Top Emission AMOLED Display on Plastic Film and Its Bending Properties,", SID Digest '09 : SID International Symposium Digest of Technical Papers, May 31, 2009, pp. 983-985.

Sakata.J et al., "Development of 4.0-in. AMOLED Display With Driver Circuit Using Amorphous In—Ga—Zn-Oxide TFTS,", IDW '09 : Proceedings of the 16th International Display Workshops, 2009, pp. 689-692.
Park.J et al., "Amorphous Indium-Gallium-Zinc Oxide TFTS and Their Application for Large Size AMOLED,", AM-FPD '08 Digest of Technical Papers, Jul. 2, 2008, pp. 275-278.
Park.S et al., "Challenge to Future Displays: Transparent AM-OLED Driven by PEALD Grown ZNO TFT,", IMID '07 Digest, 2007, pp. 1249-1252.
Godo.H et al., "Temperature Dependence of Characteristics and Electronic Structure for Amorphous In—Ga—Zn-Oxide TFT,", AM-FPD '09 Digest of Technical Papers, Jul. 1, 2009, pp. 41-44.
Osada.T et al., "Development of Driver-Integrated Panel Using Amorphous In—Ga—Zn-Oxide TFT,", AM-FPD '09 Digest of Technical Papers, Jul. 1, 2009, pp. 33-36.
Hirao.T et al., "Novel Top-Gate Zinc Oxide Thin-Film Transistors (ZNO TFTS) for AMLCDS,", Journal of the SID, 2007, vol. 15, No. 1, pp. 17-22.
Hosono.H, "68.3:Invited Paper:Transparent Amorphous Oxide Semiconductors for High Performance TFT,", SID Digest '07 : SID International Symposium Digest of Technical Papers, 2007, vol. 38, pp. 1830-1833.
Godo.H et al.; "P-9:Numerical Analysis on Temperature Dependence of Characteristics of Amorphous In—Ga—Zn-Oxide TFT,", SID Digest '09 : SID International Symposium Digest of Technical Papers, May 31, 2009, pp. 1110-1112.
Ohara.H et al., "21.3:4.0 in. QVGA AMOLED Display Using In—Ga—Zn-Oxide TFTS With a Novel Passivation Layer,", SID Digest '09 : SID International Symposium Digest of Technical Papers, May 31, 2009, pp. 284-287.
Miyasaka.M, "SUFTLA Flexible Microelectronics on Their Way to Business,", SID Digest '07 : SID International Symposium Digest of Technical Papers, 2007, vol. 38, pp. 1673-1676.
Chern.H et al., "An Analytical Model for the Above-Threshold Characteristics of Polysilicon Thin-Film Transistors,", IEEE Transactions on Electron Devices, Jul. 1, 1995, vol. 42, No. 7, pp. 1240-1246.
Kikuchi.H et al., "39.1:Invited Paper:Optically Isotropic Nano-Structured Liquid Crystal Composites for Display Applications,", SID Digest '09 : SID International Symposium Digest of Technical Papers, May 31, 2009, pp. 578-581.
Asaoka.Y et al., "29.1:Polarizer-Free Reflective LCD Combined With Ultra Low-Power Driving Technology,", SID Digest '09 : SID International Symposium Digest of Technical Papers, May 31, 2009, pp. 395-398.
Lee.H et al., "Current Status of, Challenges to, and Perspective View of AM-OLED ,", IDW '06 : Proceedings of the 13th International Display Workshops, Dec. 7, 2006, pp. 663-666.
Kikuchi.H et al., "62,2:Invited Paper:Fast Electro-Optical Switching in Polymer-Stabilized Liquid Crystalline Blue-Phases for Display Application,", SID Digest '07 : SID International Symposium Digest of Technical Papers, 2007, vol. 38, pp. 1737-1740.
Nakamura.M, "Synthesis of Homologous Compound with New Long-Period structure,", NIRIM Newsletter, Mar. 1, 1995, vol. 150, pp. 1-4.
Kikuchi.H et al., "Polymer-Stabilized Liquid Crystal Blue Phases,", Nature Materials, Sep. 2, 2002, vol. 1, pp. 64-68.
Kimizuka.N. et al., "Spinel,YBFE2O4, and YB2FE3O7 Types of Structures for Compounds in the IN2O3 and SC2O3-A2O3-BO Systems [A; Fe, Ga, or Al; B: Mg, Mn, Fe, Ni, Cu, or, Zn] at Temperatures Over 1000° C,", Journal of Solid State Chemistry, 1985, vol. 60, pp. 382-384.
Kitzerow.H et al., "Observation of Blue Phases in Chiral Networks,", Liquid Crystals, 1993, vol. 14, No. 3, pp. 911-916.
Costello.M et al., "Electron Microscopy of a Cholesteric Liquid Crystal and Its Blue Phase,", Phys. Rev. A (Physical Review. A), May 1, 1984, vol. 29, No. 5; pp. 2957-2959.
Meiboom.S et al, "Theory of the Blue Phase of Cholesteric Liquid Crystals,", Phys. Rev.Lett. (Physical Review Letters), May 4, 1981, vol. 46, No. 18, pp. 1216-1219.
Park.Sang-Hee et al., "42.3: Transparent ZnO Thin Film Transistor for the Application of High Aperture Ratio Bottom Emission AM- OLED Display,", SID Digest '08 : SID International Symposium Digest of Technical Papers, May 20, 2008, vol. 39, pp. 629-632.

Orita.M et al., "Mechanism of Electrical Conductivity of Transparent InGaZnO4,", Phys. Rev. B (Physical Review. B), Jan. 15, 2000, vol. 61, No. 3, pp. 1811-1816.

Nomura.K et al., "Amorphous Oxide Semiconductors for High-Performance Flexible Thin-Film Transistors,", Jpn. J. Appl. Phys. (Japanese Journal of Applied Physics), 2006, vol. 45, No. 5B, pp. 4303-4308.

Janotti.A et al., "Native Point Defects in ZnO,", Phys. Rev. B (Physical Review. B), Oct. 4, 2007, vol. 76, No. 16, pp. 165202-1-165202-22.

Park.J et al., "Electronic Transport Properties of Amorphous Indium-Gallium-Zinc Oxide Semiconductor Upon Exposure to Water,", Appl. Phys. Lett. (Applied Physics Letters), 2008, vol. 92, pp. 072104-1-072104-3.

Hsieh.H et al., "P-29:Modeling of Amorphous Oxide Semiconductor Thin Film Transistors and Subgap Density of States,", SID Digest '08 : SID International Symposium Digest of Technical Papers, 2008, vol. 39, pp. 1277-1280.

Janotti.A et al., "Oxygen Vacancies in ZnO,", Appl. Phys. Lett. (Applied Physics Letters), 2005, vol. 87, pp. 122102-1-122102-3.

Oba.F et al., "Defect energetics in ZnO: A hybrid Hartree-Fock density functional study,", Phys. Rev. B (Physical Review. B), 2008, vol. 77, pp. 245202-1-245202-6.

Orita.M et al., "Amorphous transparent conductive oxide InGaO3(ZnO)m (m<4):a Zn4s conductor,", Philosophical Magazine; 2001, vol. 81, No. 5, pp. 501-515.

Hosono.H et al., "Working hypothesis to explore novel wide band gap electrically conducting amorphous oxides and examples,", J. Non-Cryst. Solids (Journal of Non-Crystalline Solids), 1996, vol. 198-200, pp. 165-169.

Mo.Y et al., "Amorphous Oxide TFT Backplanes for Large Size AMOLED Displays,", IDW '08 : Proceedings of the 6th International Display Workshops, Dec. 3, 2008, pp. 581-584.

Kim.S et al., "High-Performance oxide thin film transistors passivated by various gas plasmas,", 214th ECS Meeting, 2008, No. 2317, ECS.

Clark.S et al., "First Principles Methods Using CASTEP,", Zeitschrift fur Kristallographie, 2005, vol. 220, pp. 567-570.

Lany.S et al., "Dopability, Intrinsic Conductivity, and Nonstoichiometry of Transparent Conducting Oxides,", Phys. Rev. Lett. (Physical Review Letters), Jan. 26, 2007, vol. 98, pp. 045501-1-045501-4.

Park.J et al., "Dry etching of ZnO films and plasma-induced damage to optical properties,", J. Vac. Sci. Technol. B (Journal of Vacuum Science & Technology B), Mar. 1, 2003, vol. 21, No. 2, pp. 800-803.

Oh.M et al., "Improving the Gate Stability of ZnO Thin-Film Transistors With Aluminum Oxide Dielectric Layers,", J. Electrochem. Soc. (Journal of the Electrochemical Eng.Society), 2008, vol. 155, No. 12, pp. H1009-H1014.

Ueno.K et al., "Field-Effect Transistor on SrTiO3 With Sputtered Al2O3 Gate Insulator,", Appl. Phys. Lett. (Applied Physics Letters), Sep. 1, 2003, vol. 83, No. 9, pp. 1755-1757.

OXYGEN DIFFUSION EVALUATION METHOD OF OXIDE FILM STACKED BODY

BACKGROUND OF THE INVENTION

1. Field of the Invention

One embodiment of the present invention relates to an evaluation method of an oxide material, and for example relates to an evaluation method of oxygen behavior in a structure body in which oxide films are stacked.

2. Description of the Related Art

A technique by which transistors are formed using semiconductor thin films formed over a substrate having an insulating surface has been attracting attention. Such transistors are applied to a wide range of electronic devices such as an integrated circuit (IC) or an image display device (display device). As materials of semiconductor thin films applicable to the transistors, silicon-based semiconductor materials have been widely used, but oxide semiconductors have been attracting attention as alternative materials.

For example, disclosed is a transistor whose active layer is formed using an amorphous oxide containing indium (In), gallium (Ga), and zinc (Zn) and having an electron carrier concentration of less than $10^{18}/cm^3$ (see Patent Document 1).

A transistor including an oxide semiconductor is known to have a problem of low reliability because of high possibility of fluctuation in electrical characteristics, although the transistor including an oxide semiconductor can operate at higher speed than a transistor including amorphous silicon and can be manufactured more easily than a transistor including polycrystalline silicon. For example, the threshold voltage of the transistor fluctuates between before and after a bias-temperature test (BT test).

[REFERENCE]

[Patent Document 1] Japanese Published Patent Application No. 2006-165528

SUMMARY OF THE INVENTION

Experience shows that, in a film containing oxygen as a main component, an excess or deficiency of trace amounts of oxygen with respect to a stoichiometric composition, or the like affects properties of the film. However, when the trace amounts of oxygen in the film containing oxygen as a main component are evaluated, in the existing quantitative analysis method, uncertainty of several atomic % is included in determination precision. Therefore, it has been difficult to precisely evaluate an effect of the excess or deficiency of trace amounts of oxygen in the film containing oxygen as a main component, or the like. Thus, an evaluation method by which the increase and decrease of trace amounts of oxygen in the film containing oxygen as a main component can be compared is proposed.

Further, an object is to evaluate the oxygen behavior in an oxide semiconductor film.

According to one embodiment of the present invention, an oxygen diffusion evaluation method of an oxide film stacked body includes the steps of: measuring a quantitative value of one of oxygen isotopes of a substrate including a first oxide film and a second oxide film which has an existence proportion of an oxygen isotope different from an existence proportion of an oxygen isotope in the first oxide film, in a depth direction, by secondary ion mass spectrometry; and evaluating the one of the oxygen isotopes diffused from the first oxide film to the second oxide film.

Note that the ordinal numbers such as "first" and "second" in this specification are used for convenience and do not denote the order of steps or the stacking order of layers. In addition, the ordinal numbers in this specification do not denote particular names which specify the present invention.

Further, according to one embodiment of the present invention, the first oxide and the second oxide can be replaced by each other.

In addition, one embodiment of the present invention is an oxygen diffusion evaluation method of an oxide film stacked body in which the one of the oxygen isotopes is an oxygen atom with a mass number of 18.

In this specification, an oxygen atom with a mass number of 18 is referred to as $^{18}O$. In addition, an oxygen molecule containing $^{18}O$ is referred to as $^{18}O_2$. Other isotope atoms and other molecules containing isotope atoms are described in a similar way. Although naturally there is an oxygen molecule containing $^{18}O$ and an oxygen atom with a mass number of 16 ($^{16}O$), description thereof is omitted in this specification for brevity.

In this specification, $^{18}O$ is mainly used as one of oxygen isotopes for description. However, one embodiment of the present invention is not always limited to $^{18}O$, and for example, $^{18}O$ can be replaced by an oxygen atom with a mass number of 17 ($^{17}O$) or $^{16}O$.

Further, although this specification refers to an oxygen diffusion evaluation method of an oxide film stacked body, the oxygen diffusion evaluation method can be employed for an evaluation method of an element with a stable isotope such as hydrogen, nitrogen, sulfur, or carbon.

Here, the average oxygen isotope ratio in nature is as follows: $^{16}O$ is 99.762 atomic %, $^{17}O$ is 0.037 atomic %, and $^{18}O$ is 0.204 atomic %. The above isotope ratio might have a margin of error of approximately 0.1 atomic %. It is needless to say that the present invention may be applied to the case where the isotope ratio deviates from the above isotope ratio.

From the above ratio, it is found that $^{16}O$ is 489 times as much as $^{18}O$ in nature. That is, $^{16}O$ is 489 times as much as $^{18}O$ in a normal oxide whose isotope ratio is not intentionally controlled.

For example, the first oxide film is an oxide semiconductor film or an oxide insulating film. In addition, the second oxide film is an oxide semiconductor film or an oxide insulating film.

When $^{18}O$ is contained in the first oxide film at a higher concentration than that of the second oxide film, the first oxide film is used as a supply source of $^{18}O$ and the diffusion of $^{18}O$ to the second oxide film can be evaluated if there is a sufficient difference in the content of $^{18}O$ in the first oxide film and that in the second oxide film. Depending on a diffusion coefficient, heat needs to be applied to some extent for the evaluation of $^{18}O$ diffusion in many cases.

At this time, the $^{18}O$ diffusion length x and the $^{18}O$ surface concentration $C_S$ can be estimated by SIMS in accordance with the applied temperature T and time t. Here, x is a distance from a surface (a distance between the second oxide film and an interface between the first oxide film and the second oxide film).

When Formula 1 is used, a diffusion coefficient D can be derived from the estimated $^{18}O$ diffusion length x and $^{18}O$ surface concentration $C_S$.

$$C(x, t) = C_S \cdot erfc\left(\frac{x}{2\sqrt{Dt}}\right) \qquad \text{[FORMULA 1]}$$

Here, when the diffusion coefficient D is derived under several conditions of temperature T to be applied, the diffusion coefficient D can be expressed by Formula 2; therefore, activation energy $E_a$ can be derived as will be described later.

$$D = D_0 \cdot exp\left(\frac{-E_a}{kt}\right) \quad \text{[FORMULA 2]}$$

Here, $D_0$ denotes a frequency factor and k denotes a Boltzmann constant.

By taking natural logarithms of both sides of Formula 2, Formula 3 can be given.

$$\ln D = \ln D_0 - \frac{E_a}{k} \cdot \frac{1}{T} \quad \text{[FORMULA 3]}$$

In other words, the slope of a line in which lnD is plotted with respect to the reciprocal number of T is $-(E_a/k)$, and an intercept is $\ln D_0$, so that the activation energy $E_a$ and the frequency factor $D_0$ can be derived.

According to one embodiment of the present invention, the oxygen diffusion in the film containing oxygen as a main component can be evaluated.

In addition, the increase and decrease of trace amounts of oxygen in the oxide semiconductor film can be evaluated when one embodiment of the present invention is applied to the oxide semiconductor film.

DETAILED DESCRIPTION OF THE INVENTION

Hereinafter, embodiments of the present invention will be described in detail with reference to the accompanying drawings. However, the present invention is not limited to the description below and it is easily understood by those skilled in the art that the mode and details can be changed in various ways. Therefore, the present invention is not construed as being limited to description of the embodiments described below. In describing structures of the present invention with reference to the drawings, the same reference numerals are used in common for the same portions in different drawings. Note that the same hatch pattern is applied to similar parts, and the similar parts are not especially denoted by reference numerals in some cases.

In this embodiment, a method for evaluating the oxygen diffusion from an oxide film to an oxide film adjacent to the oxide film will be described.

Further, in some cases, charge is generated due to oxygen deficiency in the oxide semiconductor film. In general, when oxygen deficiency is caused in an oxide semiconductor film, part of the oxygen deficiency becomes a donor and generates an electron which is a carrier. As a result, the threshold voltage of the transistor including an oxide semiconductor shifts in the negative direction. Note that in this specification, threshold voltage refers to a gate voltage which is needed to turn on the transistor. "Gate voltage" refers to a potential difference between a source and a gate when the potential of the source is used as a reference potential.

For example, in a transistor including an oxide semiconductor, when oxygen is supplied from an insulating film which is a base to an oxide semiconductor film, an effect of the charge generated due to the operation of the transistor or the like can be reduced.

In this manner, the variations in the electrical characteristics of the transistor due to oxygen deficiency of the oxide semiconductor film become a problem in some cases. However, in evaluation of oxygen deficiency, there was no existing simple evaluation method, and it has been necessary to comprehensively evaluate the oxygen deficiency in view of results such as a circumstantial evidence or a calculation result.

For example, uncertainty of plus or minus 5 atomic % accompanies a quantitative analysis of oxygen in an oxide film by Rutherford back scattering spectrometry (RBS). The RBS has a certain precision of a quantitative analysis of a heavy metal; however, the RBS is not suitable for a quantitative analysis of oxygen because the precision is decreased as a lower-mass element is used. In addition, uncertainty of plus or minus 0.1 weight % accompanies a quantitative analysis of oxygen in the oxide film by an electron probe X-ray micro analyzer (EPMA). The EPMA is an analysis method with relatively high determination precision; however, the thickness of the oxide film needs to be greater than or equal to 1 μm, and an obtained quantitative value is an average value in a measurement range; therefore, the EPMA is inappropriate for evaluation of oxygen in a thin film used for a transistor. In addition, in an X-ray photoelectron spectroscopy (XPS), an analysis is performed while a film is etched, so that it is possible to perform a quantitative analysis in a depth direction; however, uncertainty of plus or minus 1 atomic % accompanies a quantitative analysis of oxygen. In other words, by these quantitative analysis methods, the increase and decrease of trace amounts of oxygen in the thin film cannot be described.

In general, the quantitative analysis of trace amounts of oxygen is performed using secondary ion mass spectrometry (SIMS). Although the SIMS is suitable for a microanalysis, it is difficult to evaluate a minute increase and decrease in a main component which is contained at greater than or equal to $1 \times 10^{22}$ atoms/cm$^3$.

Thus, an oxygen diffusion evaluation method of an oxide film stacked body using one of oxygen isotopes is proposed so that the increase and decrease of trace amounts of oxygen in the film containing oxygen as a main component can be compared.

A sample in which the increase and decrease of trace amounts of oxygen can be compared is described with reference to FIG. 1. The sample includes a substrate 100, a first oxide film 102 over the substrate 100, and a second oxide film 104 over the first oxide film 102 (see FIG. 1).

Here, one of the first oxide film 102 and the second oxide film 104 includes one of oxygen isotopes at higher concentration than the ratio of the oxygen isotope existing in nature. Preferably, one of the first oxide film 102 and the second oxide film 104 includes the oxygen isotope at greater than or equal to $1 \times 10^{21}$ atoms/cm$^3$. As the oxygen isotopes, $^{16}$O, $^{17}$O, and $^{18}$O are known.

For example, an oxide insulating film is used for the first oxide film 102. As a material of the oxide insulating film, silicon oxide, aluminum oxide, titanium oxide, vanadium oxide, chromium oxide, manganese oxide, iron oxide, cobalt oxide, nickel oxide, copper oxide, yttrium oxide, zirconium oxide, niobium oxide, molybdenum oxide, lanthanum oxide, hafnium oxide, tantalum oxide, tungsten oxide, cerium oxide, neodymium oxide, or the like is used. Alternatively, the above-described oxides may be mixed. In addition, hydrogen, nitrogen, carbon, fluorine, chlorine, bromine, iodine, helium, neon, argon, krypton, xenon, or the like may be contained.

For example, an oxide semiconductor film is used as the second oxide film 104. As a material used for the oxide semiconductor film, an In—Sn—Ga—Zn—O-based material which is a four-component metal oxide; an In—Ga—Zn—O-based material, an In—Sn—Zn—O-based material, an In—Al—Zn—O-based material, a Sn—Ga—Zn—O-based material, an Al—Ga—Zn—O-based material, or a Sn—Al—Zn—O-based material which are three-component metal oxides; an In—Zn—O-based material, a Sn—Zn—O-based material, an Al—Zn—O-based material, a Zn—Mg—O-based material, a Sn—Mg—O-based material, an In—Mg—O-based material, or an In—Ga—O-based material which are two-component metal oxides; an In—O-based material; a Sn—O-based material; a Zn—O-based material; or the like may be used. Further, silicon oxide may be contained in the above materials. Here, for example, an In—Ga—Zn—O-based material means an oxide film containing indium (In), gallium (Ga), and zinc (Zn), and there is no particular limitation on the composition ratio. Further, the In—Ga—Zn—O-based oxide semiconductor may contain an element other than In, Ga, and Zn.

For the oxide semiconductor film, a thin film using a material represented by the chemical formula, $InMO_3(ZnO)_m$ (m>0), is formed. Here, M represents one or more metal elements selected from Ga, Al, Mn, and Co. For example, M may be Ga, Ga and Al, Ga and Mn, Ga and Co, or the like.

Here, the first oxide film 102 and the second oxide film 104 may be replaced by each other, as appropriate. Further, in this embodiment, an oxide insulating film is used for the first oxide film 102 and an oxide semiconductor film is used for the second oxide film 104; however, one embodiment of the present invention is not limited to this. For example, an oxide semiconductor film may be used as the first oxide film 102, and an oxide semiconductor film may be used for the second oxide film 104. The same applies to the case where an oxide insulating film is used instead of an oxide semiconductor film.

Although not illustrated, a protective film may be provided over the second oxide film. With the protective film, degas of the second oxide film can be suppressed. As the protective film, a silicon nitride film, a silicon nitride oxide film, an aluminum oxide film, an aluminum nitride film, or the like can be used.

Alternatively, the first oxide film 102 and the second oxide film 104 may be formed using not only an oxide but also a nitride, a sulfide, a fluoride, a chloride, a selenium compound, an organic compound, others compounds, or the like. In that case, a deposition gas having an isotope which is used in forming the first oxide film 102 and the second oxide film 104 which are described later may be selected as appropriate.

There is no particular limitation on the property of a material and the like of the substrate 100 as long as the material has heat resistance enough to withstand at least heat treatment to be performed later. For example, a glass substrate, a ceramic substrate, a quartz substrate, a sapphire substrate, or the like can be used as the substrate 100. Alternatively, a single crystal semiconductor substrate or a polycrystalline semiconductor substrate made of silicon, silicon carbide, or the like, a compound semiconductor substrate made of silicon germanium or the like, an SOI substrate, or the like may be used as the substrate 100. Still alternatively, any of these substrates further provided with a semiconductor element may be used as the substrate 100.

Here, SIMS is performed on the first oxide film 102 and the second oxide film 104, quantitative analyses of the concentration of oxygen isotopes included in each of the first oxide film 102 and the second oxide film 104 in a depth direction are performed. Note that a cesium primary ion ($Cs^+$) may be used as a primary ion species.

Thus, it is possible to evaluate the distance, the density, or the like of one oxygen isotope which has higher existence proportion than a naturally-occurring oxygen isotope included in the first oxide film 102 and which is diffused in the second oxide film 104. Alternatively, it is possible to evaluate the distance, the density, or the like of one oxygen isotope which has higher existence proportion than a naturally-occurring oxygen isotope included in the second oxide film 104 and which is diffused in the first oxide film 102.

Figure 1:
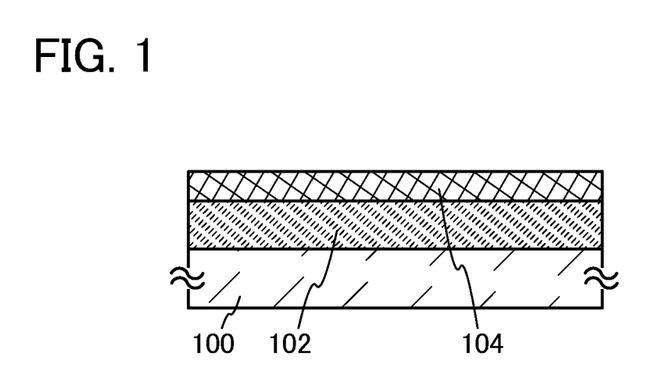
FIG. 1 illustrates a cross-sectional structure of a sample for describing one embodiment.

Further alternatively, it may be possible to evaluate the distance, the density, or the like of one oxygen isotope which has higher existence proportion than a naturally-occurring oxygen isotope included in the first oxide film 102 and which is diffused in the second oxide film 104 when the laminate illustrated in FIG. 1 is subjected to heat treatment for a given period. Further alternatively, it may be possible to evaluate the distance, the density, or the like of one oxygen isotope which has higher existence proportion than a naturally-occurring oxygen isotope included in the second oxide film 104 and which is diffused in the first oxide film 102.

At this time, when Formula 1 is used, the diffusion coefficient D can be derived from the time t and temperature T of the heat treatment. In addition, when Formula 3 is used, the activation energy $E_a$ and the frequency factor $D_0$ can be derived from plots of the diffusion coefficient D and the reciprocal number of temperature T.

Next, a manufacturing method of the laminate illustrated in FIG. 1 is described.

First, the first oxide film 102 is formed by a film formation method such as a sputtering method, a molecular beam epitaxy (MBE) method, a CVD method, a pulsed laser deposition method, or an atomic layer deposition (ALD) method. Alternatively, any method may be used as long as it is a film formation method by which one oxygen isotope which has higher existence proportion than a naturally-occurring oxygen isotope can be included in the first oxide film 102.

For example, in the case where an aluminum oxide film is formed as the first oxide film 102 by a sputtering method, a reactive sputtering method in which after 10 sccm of an argon gas as a deposition gas and 40 sccm of $^{18}O_2$ as an oxygen gas are introduced into a sputtering chamber and the pressure is adjusted to 0.4 Pa, an electric power of 1 kW from a pulsed DC power source is applied to an aluminum target using the deposition gas, may be used. At this time, the temperature of the substrate over which a film is deposited may be room temperature.

In the case where a silicon oxynitride film is formed as the first oxide film 102 by a plasma-enhanced CVD method which is a kind of a CVD method, after 25 sccm of a silane gas as a deposition gas and 1000 sccm of $N_2{}^{18}O$ as a nitrous oxide gas are introduced and the pressure is adjusted to 133.3 Pa, an electric power of 35 W from an RF power source is applied to an electrode, so that a gas phase reaction and a substrate surface reaction are generated; accordingly, a film may be deposited. At this time, the temperature of the substrate over which a film is deposited and the temperature of the electrode are each 200° C.

Alternatively, without limitation to the case of using the above-described film formation method, $^{18}O$ may be contained in a deposition gas at greater than or equal to 1 atomic %.

Note that here, silicon oxynitride includes more oxygen than nitrogen, and in the case where measurements are conducted using RBS and hydrogen forward scattering spectrometry (HFS), silicon oxynitride preferably includes oxygen, nitrogen, and silicon at concentrations ranging from 50 atomic % to 70 atomic %, 0.5 atomic % to 15 atomic %, and 25 atomic % to 35 atomic %, respectively. Further, silicon nitride oxide includes more nitrogen than oxygen, and in the case where measurements are conducted using RBS and HFS, silicon nitride oxide preferably includes oxygen, nitrogen, silicon, and hydrogen at concentrations ranging from 5 atomic % to 30 atomic %, 20 atomic % to 55 atomic %, 25 atomic % to 35 atomic %, and 10 atomic % to 30 atomic %, respectively. Note that percentages of nitrogen, oxygen, silicon, and hydrogen fall within the ranges given above, where the total number of atoms contained in the silicon oxynitride or the silicon nitride oxide is defined as 100 atomic %.

Here, in the case where the substrate, the first oxide film 102, and the second oxide film 104 are heated, heating may be performed using a resistance heating element or the like, for example. Alternatively, heat conduction or heat radiation from a medium such as a heated gas may be used for heating. For example, a rapid thermal anneal (RTA) apparatus such as a gas rapid thermal anneal (GRTA) apparatus or a lamp rapid thermal anneal (LRTA) apparatus can be used. An LRTA apparatus is an apparatus for heating an object to be processed by radiation of light (an electromagnetic wave) emitted from a lamp such as a halogen lamp, a metal halide lamp, a xenon arc lamp, a carbon arc lamp, a high-pressure sodium lamp, or a high-pressure mercury lamp. A GRTA apparatus is an apparatus for performing heat treatment using a high-temperature gas. An inert gas is used as a gas.

Through the above process, the laminate illustrated in FIG. 1 can be formed.

This embodiment makes it possible to evaluate the oxygen diffusion from the oxide film to the oxide film adjacent thereto.

EXAMPLE 1

In this example, a silicon oxide film which is formed by sputtering a quartz target with the use of $^{18}O_2$ and $O_2$ as a deposition gas will be described. Note that the simple expression "$O_2$" means oxygen including an isotope at a naturally-occurring ratio.

As a deposition gas, 25 sccm of an argon gas and 25 sccm of an oxygen gas were used. At this time, the total oxygen gas flow was constant, while the mixture ratio of $^{18}O_2$ and $O_2$ in the oxygen gas was changed. Specifically, with the ratio of ($^{18}O_2/^{18}O_2+O_2$) set to 0 volume %, 20 volume %, 40 volume %, 60 volume %, 80 volume %, and 100 volume %, a quartz target was sputtered to form a silicon oxide film with a thickness of 300 nm. Then, the average concentrations of $^{18}O$ and $^{16}O$ contained in the silicon oxide film were evaluated by SIMS (see FIG. 2). Note that a cesium primary ion was used as a primary ion species. The average concentrations of $^{18}O$ and $^{16}O$ were calculated ignoring 50-nm depth from the surface of the silicon oxide film and the interface between the substrate and the silicon oxide film. The film formation conditions of the silicon oxide film were as follows.
Film formation method: RF sputtering method
Target: quartz target
Deposition gas: Ar (25 sccm), $^{18}O_2+O_2$ (a total of 25 sccm)
Electric power: 1.5 kW (13.56 MHz)
Pressure: 0.4 Pa
T–S distance: 60 mm
Substrate temperature in film formation: 100° C.

Figure 2:
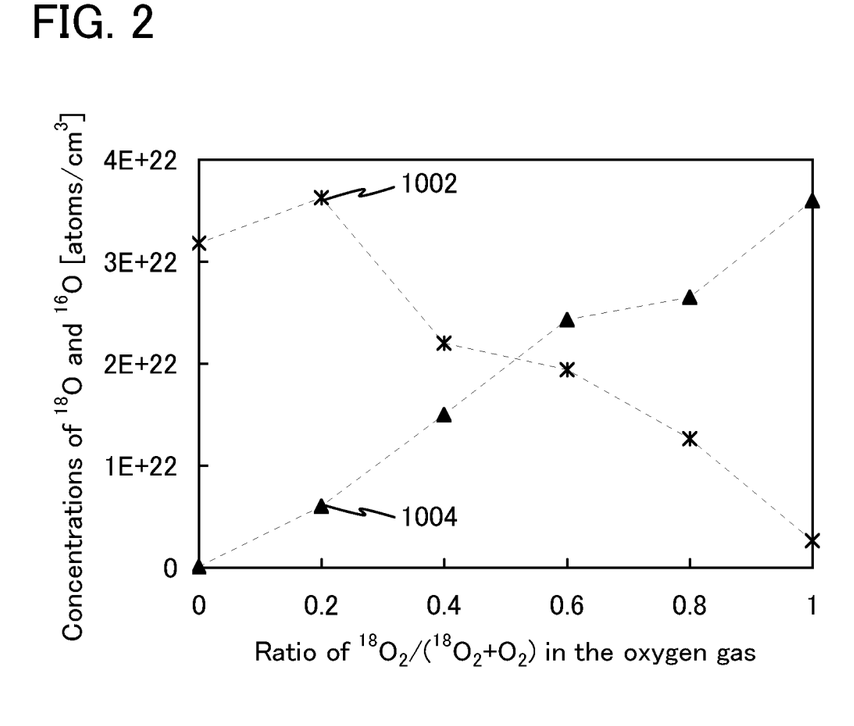
FIG. 2 illustrates the oxygen concentration.

In FIG. 2, a symbol 1002 denotes the concentration of $^{16}O$, and a symbol 1004 denotes the concentration of $^{18}O$. It is found that, as the ratio of ($^{18}O_2/^{18}O_2+O_2$) in the oxygen gas was increased, the concentration of $^{18}O$ in the film was increased in a linear function manner while the concentration of $^{16}O$ was decreased in a linear function manner.

According to this example, it is found that the ratio of $^{18}O$ and $^{16}O$ in the silicon oxide film which is formed by sputtering a quartz target with the use of $^{18}O_2$ and $O_2$ as a deposition gas is determined in accordance with the ratio of ($^{18}O_2/^{18}O_2+O_2$) in the oxygen gas.

EXAMPLE 2

In this example, an example in which oxygen diffused from a silicon oxide film to an oxide semiconductor film is evaluated will be described.

Note that $^{18}O$ is contained in the first oxide film 102 by a method described in Example 2 in order to evaluate the oxygen diffusion to the oxide semiconductor film.

In this example, in samples 1 to 5, $^{18}O$ in a depth direction was analyzed by SIMS. Note that a cesium primary ion was used as a primary ion species.

A method for manufacturing each sample is described here.

First, a silicon oxide film including $^{18}O$ was formed over a quartz substrate. The film formation conditions of the silicon oxide film were as follows.
Film formation method: RF sputtering method
Target: quartz target
Deposition gas: Ar (25 sccm), $^{18}O_2$ (25 sccm)
Electric power: 1.5 kW (13.56 MHz)
Pressure: 0.4 Pa
T–S distance: 60 mm
Substrate temperature in film formation: 100° C.
Thickness: 300 nm Next, an oxide semiconductor film was formed over the silicon oxide film.

The film formation conditions of the oxide semiconductor film were as follows.
Film formation method: DC sputtering method
Target: In—Ga—Zn—O ($In_2O_3$:$Ga_2O_3$:ZnO=1:1:2 [molar ratio]) target
Deposition gas: Ar (30 sccm), $O_2$ (15 sccm)
Electric power: 0.5 kW (DC)
Pressure: 0.4 Pa
T–S distance: 60 mm
Substrate temperature in film formation: 200° C.
Thickness: 100 nm Then, heat treatment is performed. The heat treatment was performed at a temperature of 250° C., 450° C., 550° C., or 650° C. under a nitrogen atmosphere for an hour. Here, the heating temperatures of the sample 2, the sample 3, the sample 4, and the sample 5 were set to 250° C., 450° C., 550° C., and 650° C., respectively. Note that heat treatment was not performed on the sample 1.

Figure 3:
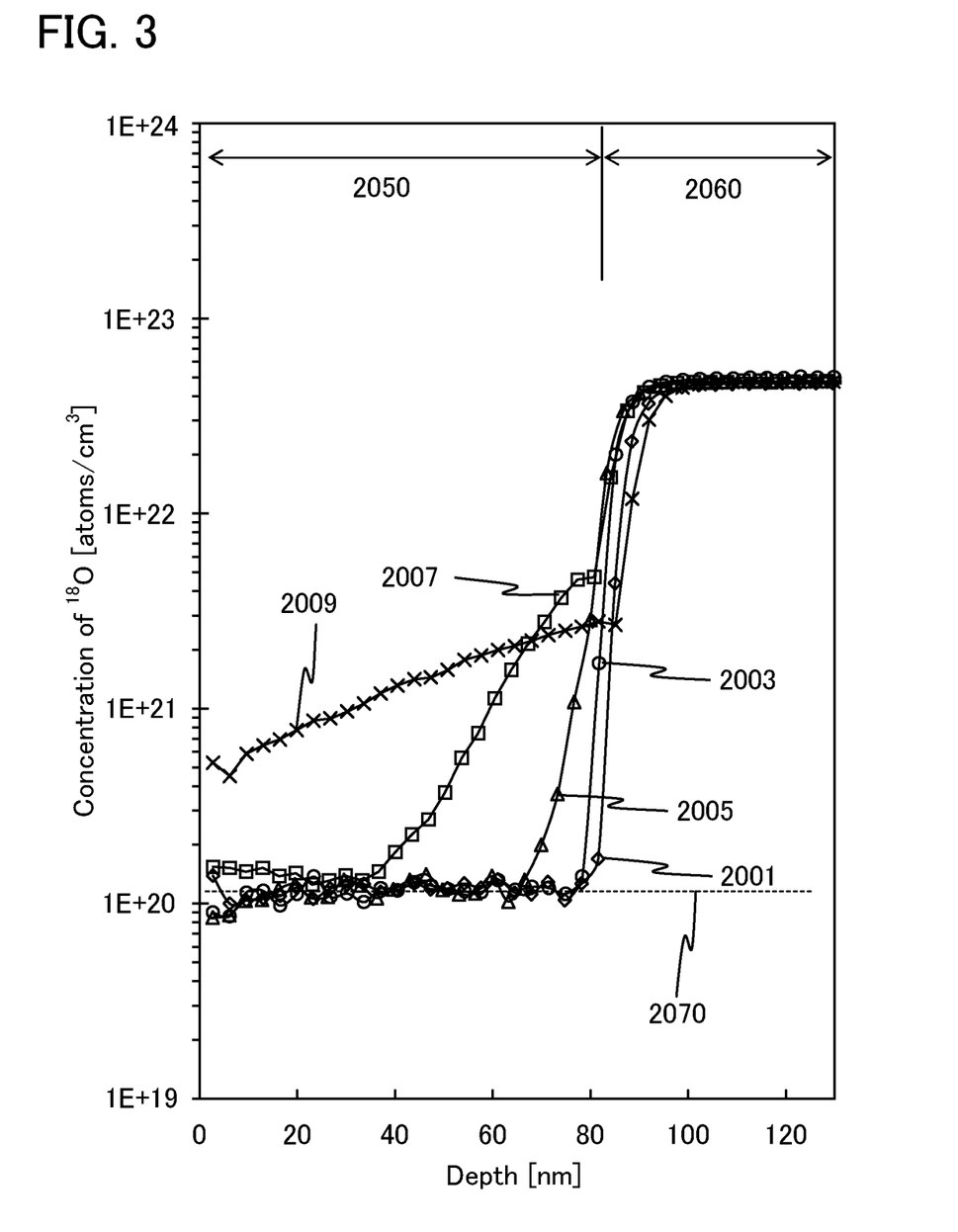
FIG. 3 illustrates the oxygen diffusion.

FIG. 3 shows results of analyzing $^{18}O$ of the samples 1 to 5 in a depth direction. A symbol 2001, a symbol 2003, a symbol 2005, a symbol 2007, and a symbol 2009 show the sample 1, the sample 2, the sample 3, the sample 4, and the sample 5 respectively. In addition, a range 2050 shows the oxide semiconductor film, and a range 2060 shows the silicon oxide film.

Here, the quantitative $^{18}$O is in the range 2050. Note that a dashed line 2070 shows a quantitative lower limit of $^{18}$O in the oxide semiconductor film.

It is found that most $^{18}$O was not diffused to the oxide semiconductor film in the SIMS measurement range in the samples 1 and 2. Further, it is found that the surface concentration of $^{18}$O in the oxide semiconductor film was increased and the diffusion length was increased as the temperatures for the heat treatment of the samples 3 to 5 were sequentially increased.

Here, a diffusion coefficient was estimated assuming that the surface concentration of $^{18}$O in the silicon oxide film, which was a diffusion source of $^{18}$O, was constant; and the concentration of $^{18}$O in infinity was zero. With the above assumption, the concentration distribution of $^{18}$O in a depth direction can be expressed by Formula 1.

When fitting with experimental values was performed using Formula 1, the position of an interface between the silicon oxide film and the oxide semiconductor film, which served as a distance criterion, was determined from the position at which the silicon signal intensity significantly changed.

Here, $C_S$ denotes the surface concentration of $^{18}$O in the oxide semiconductor film; x, a distance from the surface (here, a distance between the oxide semiconductor film and an interface between the silicon oxide film and the oxide semiconductor film); D, a diffusion coefficient of $^{18}$O in the oxide semiconductor film; and t, a time of heat treatment.

Figure 4:
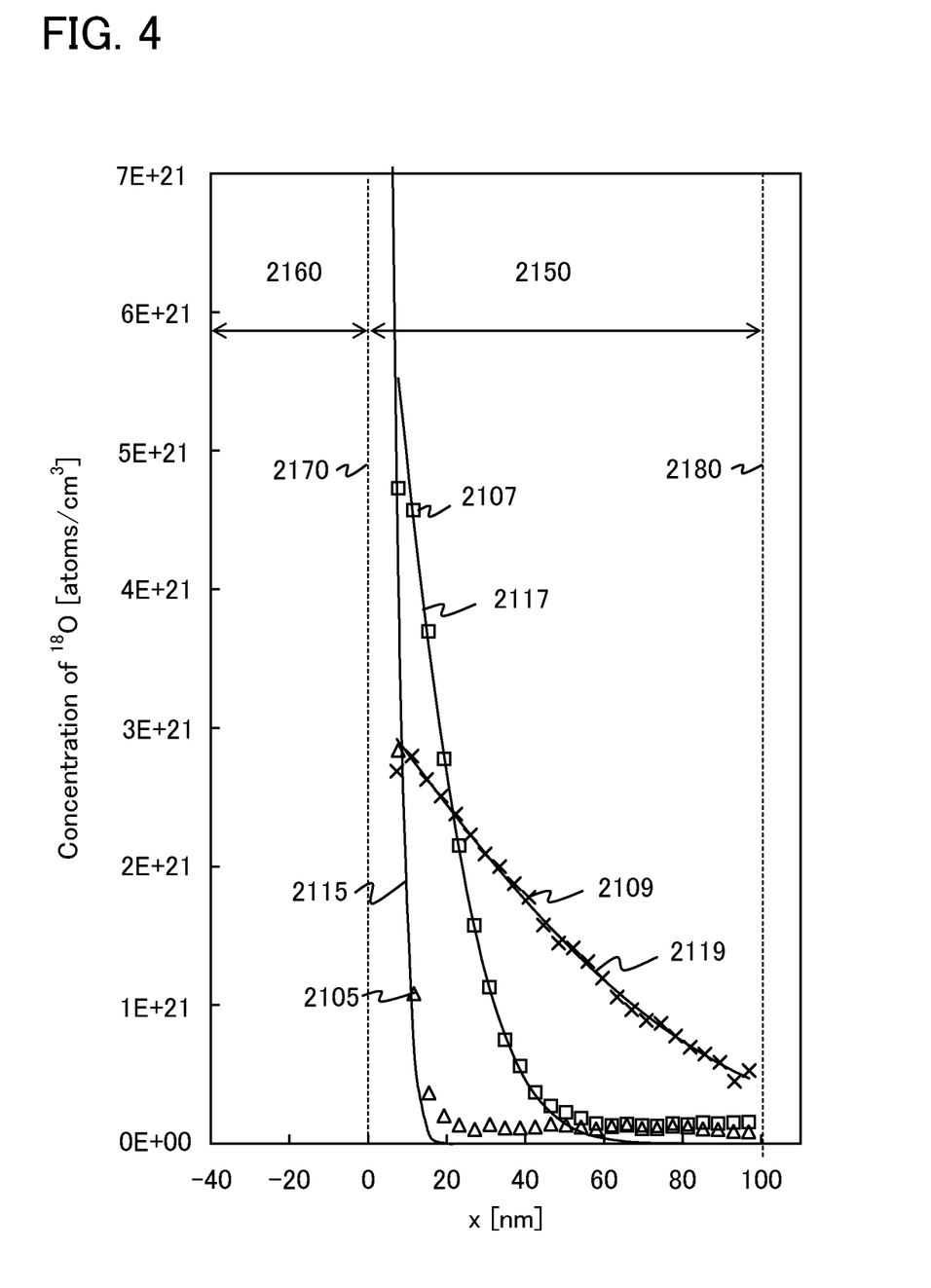
FIG. 4 is a graph for analyzing the oxygen diffusion.

FIG. 4 shows results of fitting which was performed with Formula 1. A symbol 2105, a symbol 2107, and a symbol 2109 show the concentrations of $^{18}$O of the sample 3, the sample 4, and the sample 5, respectively. Further, a solid line 2115, a solid line 2117, and a solid line 2119 show the fitting curves of the sample 3, the sample 4, and the sample 5, respectively. Here, a range 2150 shows the oxide semiconductor film, and a range 2160 shows the silicon oxide film. Here, the quantitative $^{18}$O is in the range 2150. Note that a dashed line 2170 shows an interface between the silicon oxide film and the oxide semiconductor film, and a dashed line 2180 shows a surface of the oxide semiconductor film. The obtained fitting values can reproduce the experimental values very well. Note that the fitting was not performed on the samples 1 and 2 because the diffusion cannot be confirmed in the SIMS measurement range according to FIG. 3.

From the fitting results of FIG. 4, the diffusion coefficient of $^{18}$O in the sample 3 was $3.5 \times 10^{-17}$ cm$^2$/second, the diffusion coefficient of $^{18}$O in the sample 4 was $6.3 \times 10^{-16}$ cm$^2$/second, and the diffusion coefficient of $^{18}$O in the sample 5 was $6.2 \times 10^{-15}$ cm$^2$/second.

Figure 5:
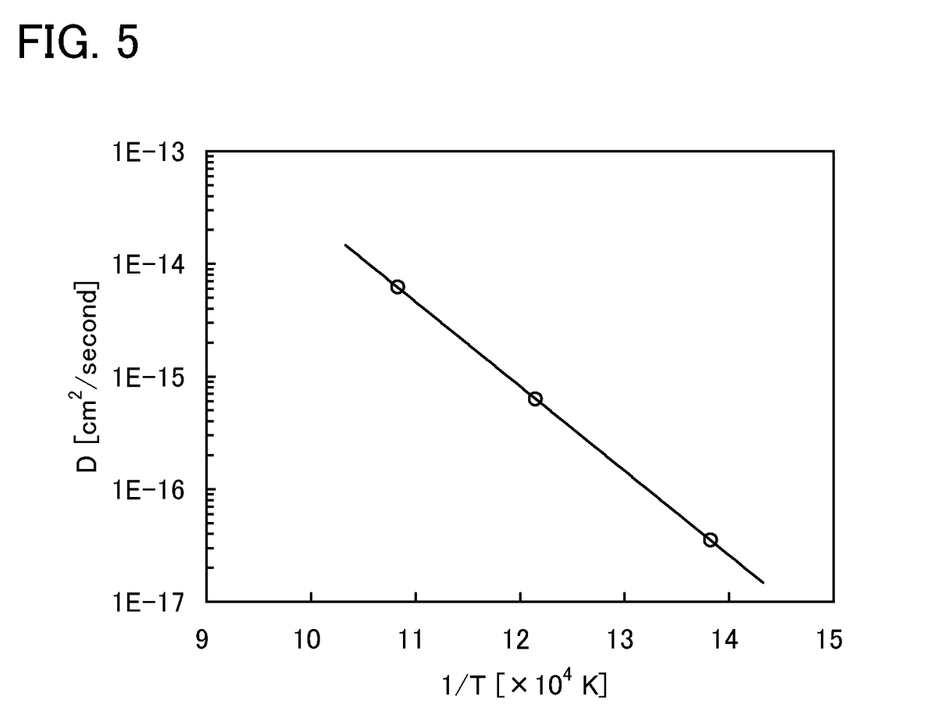
FIG. 5 is a graph in which an oxygen diffusion coefficient and the reciprocal number of temperature are plotted.

Here, from Formula 3, the natural logarithms of D and the reciprocals of T in the samples 3 to 5, which were obtained from FIG. 4, are plotted and shown in FIG. 5. When the plots of FIG. 5 are approximated, $\ln D_0$ and $-(E_a/k)$ were obtained to be $-14.304$ and $-17025$, respectively. In other words, $D_0$ was $6.16 \times 10^{-7}$ cm$^2$/second. Further, since k is $1.3807 \times 10^{-23}$ J/K, $E_a$ is $2.39 \times 10^{-19}$ J. When $E_a$ is converted into another unit, 1.49 eV can be obtained.

Through this example, it was possible to evaluate diffusion of oxygen from the silicon oxide film into the oxide semiconductor film.

In addition, when Formula 2 is used, the diffusion coefficient D at each temperature can be extrapolated and derived from the obtained frequency factor $D_0$ and the activation energy $E_a$; therefore, it is possible to describe the diffusion of oxygen which is less than or equal to the lower limit of SIMS analysis measurement.

The stable operation and characteristic improvement of the transistor including an oxide semiconductor are obtained by the diffusion of oxygen from the oxide insulating film which is a base to the oxide semiconductor layer.

Figure 6A:
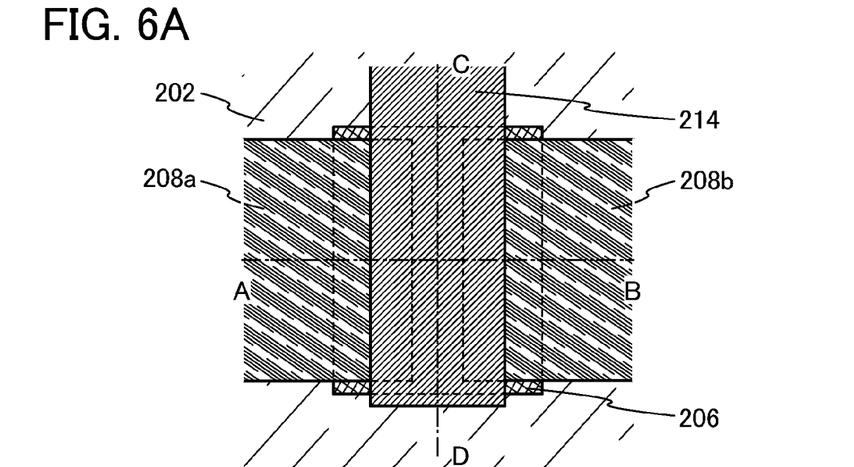
FIGS. 6A to 6C are a top view and cross-sectional views of a transistor.
Figure 6B:
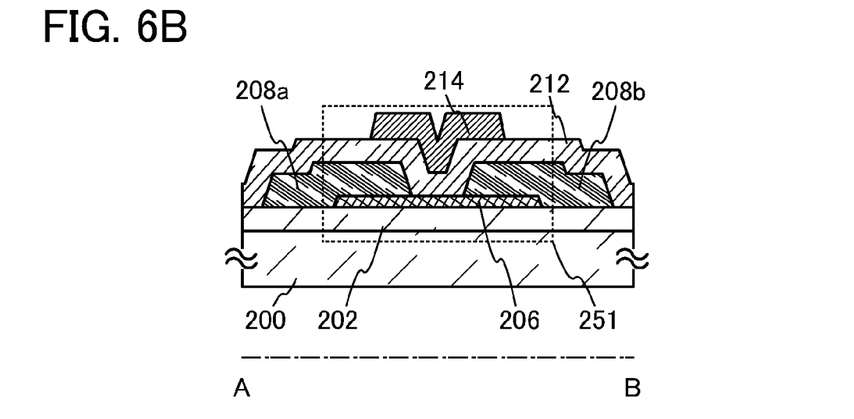
Figure 6C:
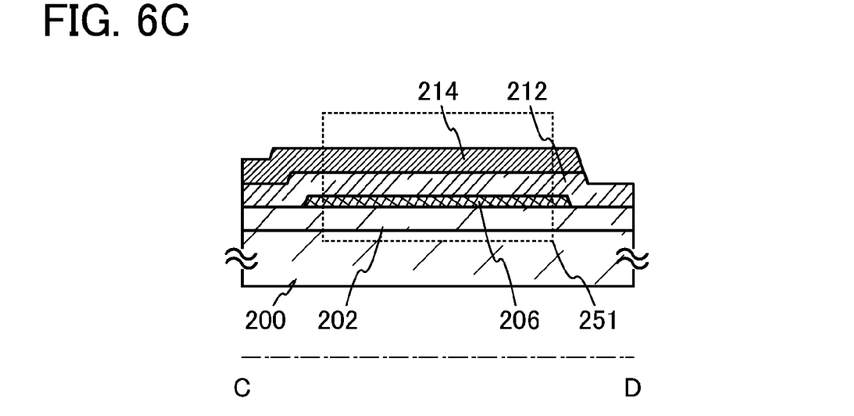

FIG. 6A is a top view of a top-gate top-contact transistor 251 including an oxide semiconductor, and FIGS. 6B and 6C are cross-sectional views thereof. Here, FIG. 6A is a top view, FIG. 6B is a cross-sectional view along A-B of FIG. 6A, and FIG. 6C is a cross-sectional view along C-D of FIG. 6A. Note that in FIG. 6A, part of components of the transistor 251 (e.g., a gate insulating film 212) are omitted for brevity.

The transistor 251 illustrated in FIGS. 6A to 6C includes a substrate 200, an oxide insulating film 202 over the substrate 200, an oxide semiconductor film 206 over the oxide insulating film 202, a pair of a source electrode 208a and a drain electrode 208b provided over the oxide semiconductor film 206, the gate insulating film 212 which covers the source electrode 208a and the drain electrode 208b and is partly in contact with the oxide semiconductor film 206, and a gate electrode 214 provided over the oxide semiconductor film 206 with the gate insulating film 212 interposed therebetween.

The silicon oxide film with a thickness of 300 nm which is described in Example 2 was used for the oxide insulating film 202. In addition, the oxide semiconductor film with a thickness of 30 nm which is described in Example 2 was used for the oxide semiconductor film 206. In Example 2, it is found that, as the heat treatment temperature of the samples is increased, the amount of oxygen diffusion from the silicon oxide film to the oxide semiconductor film is increased. The changes in various characteristics of a transistor formed by the increase in the amount of oxygen diffusion from the silicon oxide film to the oxide semiconductor film will be described below.

A tungsten film with a thickness of 100 nm was used as the material of each of the source electrode 208a, the drain electrode 208b, and the gate electrode 214.

A silicon oxynitride film with a thickness of 30 nm was used for the gate insulating film 212.

Two samples of the transistors 251 were prepared and subjected to heat treatment. The heat treatment was performed at a temperature of 250° C. or 350° C. under a nitrogen gas atmosphere for an hour. By the heat treatment, the oxygen diffusion from the oxide insulating film 202 which is a base to the oxide semiconductor film 206 occurs.

Note that the result of Example 2 shows that when oxygen diffusions at 250° C. and 350° C. are extrapolated, oxygen is diffused at greater than or equal to $1 \times 10^{17}$ atoms/cm$^3$ to a depth of 0.2 nm at 250° C. while oxygen is diffused at greater than or equal to $1 \times 10^{17}$ atoms/cm$^3$ to a depth of 3 nm at 350° C.

Figure 7A:
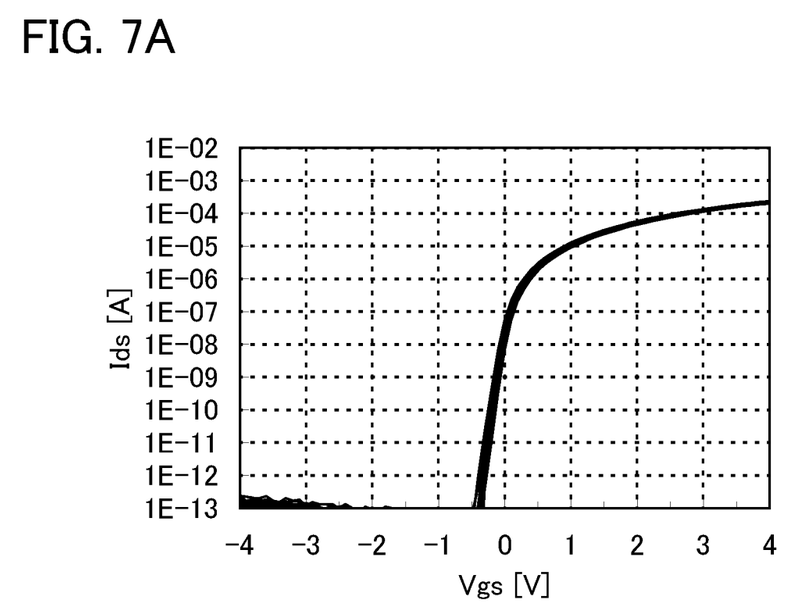
FIGS. 7A and 7B illustrate electrical characteristics of a transistor.
Figure 7B:
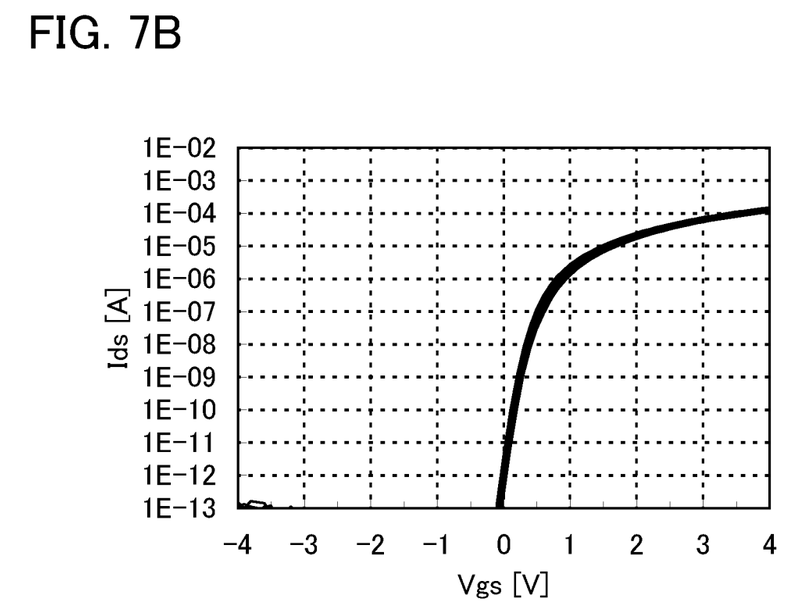

FIGS. 7A and 7B each show drain current (Ids)-gate voltage (Vgs) measurement results in the transistor of this example. Note that the measurement was performed at 25 points on a substrate surface. The measurement results of the 25 points are all shown in FIGS. 7A and 7B. The channel length L is 0.8 μm, and the channel width W is 10 μm. Note that the voltage Vds between the source electrode and the drain electrode of the transistor was set to 3 V.

FIG. 7A shows Ids-Vgs measurement results of the sample which was subjected to heat treatment at 250° C., and FIG. 7B shows Ids-Vgs measurement results of the sample which was subjected to heat treatment at 350° C. In the sample which was subjected to heat treatment at 250° C., the average threshold voltage was 0.22 V and the average current value where Vgs=0 V was $1.7 \times 10^{-8}$ A. In the sample which was subjected to heat treatment at 350° C., the average threshold voltage was 0.72 V and the average current value where Vgs=0 V was $1.2 \times 10^{-12}$ A.

In the sample in which the amount of oxygen diffusion from the oxide insulating film 202 to the oxide semiconductor film 206 was large, the threshold voltage shifted in a positive direction and the current value where Vgs=0 V was decreased. In other words, the transistor can be normally-off by the oxygen diffusion.

In this manner, the behavior of the oxygen diffusion between the oxide insulating film and the oxide semiconductor film is grasped, which contributes to the development of a transistor including an oxide semiconductor and a device related thereto, and to improvement in reliability and characteristics of the transistor and the device.

This application is based on Japanese Patent Application serial no. 2010-190577 filed with Japan Patent Office on Aug. 27, 2010, the entire contents of which are hereby incorporated by reference.

What is claimed is:

1. An oxygen diffusion evaluation method of an oxide film stacked body, comprising the steps of:
    forming a first oxide film over a substrate;
    forming a second oxide film over the first oxide film;
    heating the first oxide film and the second oxide film;
    measuring a concentration of an oxygen isotope in the second oxide film in a depth direction by secondary ion mass spectrometry after the step of the heating; and
    evaluating diffusion of the oxygen isotope from the first oxide film to the second oxide film,
    wherein an oxygen isotope ratio in the first oxide film is different from an oxygen isotope ratio in the second oxide film.

2. The oxygen diffusion evaluation method of an oxide film stacked body, according to claim 1, wherein the oxygen isotope is an oxygen atom with a mass number of 18.

3. The oxygen diffusion evaluation method of an oxide film stacked body, according to claim 1, wherein at least one of the first oxide film and the second oxide film is an oxide semiconductor film.

4. The oxygen diffusion evaluation method of an oxide film stacked body, according to claim 3, wherein the oxide semiconductor film comprises at least one of indium, gallium, and zinc.

5. The oxygen diffusion evaluation method of an oxide film stacked body, according to claim 1, wherein at least one of the first oxide film and the second oxide film is an oxide insulating film.

6. The oxygen diffusion evaluation method of an oxide film stacked body, according to claim 1, wherein the first oxide film is formed using a gas containing greater than or equal to 1 atomic % of an oxygen atom with a mass number of 18.

7. The oxygen diffusion evaluation method of an oxide film stacked body, according to claim 6, wherein the first oxide film is formed by a sputtering method.

8. The oxygen diffusion evaluation method of an oxide film stacked body, according to claim 1, further comprising the step of forming a protective film over the second oxide film.

9. The oxygen diffusion evaluation method of an oxide film stacked body, according to claim 8, wherein the protective film comprises a silicon nitride film, a silicon nitride oxide film, an aluminum oxide film, or an aluminum nitride film.

10. An oxygen diffusion evaluation method of an oxide film stacked body, comprising the steps of:
    forming a first oxide film over a substrate;
    forming a second oxide film in contact with the first oxide film;
    heating the first oxide film and the second oxide film;
    measuring a concentration of an oxygen isotope in the second oxide film in a depth direction by secondary ion mass spectrometry after the step of the heating; and
    evaluating diffusion of the oxygen isotope from the first oxide film to the second oxide film,
    wherein an oxygen isotope ratio in the first oxide film is different from an oxygen isotope ratio in the second oxide film.

11. The oxygen diffusion evaluation method of an oxide film stacked body, according to claim 10, wherein the oxygen isotope is an oxygen atom with a mass number of 18.

12. The oxygen diffusion evaluation method of an oxide film stacked body, according to claim 10, wherein at least one of the first oxide film and the second oxide film is an oxide semiconductor film.

13. The oxygen diffusion evaluation method of an oxide film stacked body, according to claim 12, wherein the oxide semiconductor film comprises at least one of indium, gallium, and zinc.

14. The oxygen diffusion evaluation method of an oxide film stacked body, according to claim 10, wherein at least one of the first oxide film and the second oxide film is an oxide insulating film.

15. The oxygen diffusion evaluation method of an oxide film stacked body, according to claim 10, wherein the first oxide film is formed using a gas containing greater than or equal to 1 atomic % of an oxygen atom with a mass number of 18.

16. The oxygen diffusion evaluation method of an oxide film stacked body, according to claim 15, wherein the first oxide film is formed by a sputtering method.

17. The oxygen diffusion evaluation method of an oxide film stacked body, according to claim 10, further comprising the step of forming a protective film over the second oxide film.

18. The oxygen diffusion evaluation method of an oxide film stacked body, according to claim 17, wherein the protective film comprises a silicon nitride film, a silicon nitride oxide film, an aluminum oxide film, or an aluminum nitride film.

* * * * *